(12) United States Patent
Ragsdale

(10) Patent No.: US 8,008,063 B2
(45) Date of Patent: Aug. 30, 2011

(54) INDIVIDUAL-CELL ELECTROPORATION USING AREA-FOCUSED ELECTRIC FIELDS

(75) Inventor: Charles W. Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 56 days.

(21) Appl. No.: 12/479,458

(22) Filed: Jun. 5, 2009

(65) Prior Publication Data

US 2009/0317883 A1 Dec. 24, 2009

Related U.S. Application Data

(60) Provisional application No. 61/075,066, filed on Jun. 24, 2008.

(51) Int. Cl.
*C12M 1/42* (2006.01)
*C12M 1/00* (2006.01)
*C12N 13/00* (2006.01)
*C12N 15/87* (2006.01)

(52) U.S. Cl. .............. 435/285.2; 435/173.1; 435/173.6; 435/460; 435/461; 204/403.01

(58) Field of Classification Search ............... 435/285.2, 435/173.1–173.6, 460, 461; 204/403.1
See application file for complete search history.

(56) References Cited

U.S. PATENT DOCUMENTS

| 6,221,665 | B1* | 4/2001 | Jaroszeski et al. | 435/450 |
| 6,315,940 | B1* | 11/2001 | Nisch et al. | 435/287.1 |
| 2003/0124713 | A1 | 7/2003 | Ragsdale | |
| 2004/0058423 | A1 | 3/2004 | Albritton et al. | |
| 2004/0197898 | A1* | 10/2004 | Nakatani et al. | 435/287.1 |
| 2007/0155015 | A1* | 7/2007 | Vassanelli et al. | 435/461 |
| 2007/0231873 | A1 | 10/2007 | Ragsdale | |
| 2007/0243523 | A1* | 10/2007 | Ionescu-Zanetti et al. | 435/4 |
| 2008/0138876 | A1 | 6/2008 | Ragsdale | |

* cited by examiner

*Primary Examiner* — Nathan A Bowers
*Assistant Examiner* — Gautam Prakash
(74) *Attorney, Agent, or Firm* — Kilpatrick, Townsend & Stockton LLP.; M. Henry Heines

(57) ABSTRACT

Electroporation is performed on a population of cells, liposomes, vesicles, or other membrane-encased structures with uniform results regardless of size variations within the population, by drawing the membrane-encased structures into micron-sized openings that contain paired electrodes. An electric potential is then imposed between the paired electrodes to permeabilize only that portion of each cell that extends into the openings and resides within the electric field focused in the area between the electrodes.

8 Claims, 3 Drawing Sheets

INDIVIDUAL-CELL ELECTROPORATION USING AREA-FOCUSED ELECTRIC FIELDS

CROSS-REFERENCE TO RELATED APPLICATION

This application claims the benefit of U.S. Provisional Patent Application No. 61/075,066, filed Jun. 24, 2008, the contents of which are incorporated herein by reference.

BACKGROUND OF THE INVENTION

1. Field of the Invention

This invention lies in the field of transfection, the process by which exogenous molecular species are inserted into membranous structures by rendering the membranes of such structures permeable on a transient basis while the structures are in contact with a liquid solution of the species, thereby allowing the species to pass through the membranes.

2. Description of the Prior Art

The transformation of cells and other membrane-encased structures by the insertion of exogenous species, including species that are hydrophilic or otherwise membrane-impermeant, is of use in certain biologic and biochemical procedures. The transformation is generically referred to as transfection, and obtaining high efficiency in the procedure is a persistent problem. High efficiency in transfection means a high proportion of successfully transformed structures with minimal loss of viability of the structures, or at least with maximal restoration of the structures' viability upon the completion of the procedure by the natural processes of the structures themselves. A common way of performing transfection is by electroporation, which is the use of an electric field as the source of energy for permeabilization of the membrane. Standard electroporation procedures are performed in bulk, i.e., on populations of cells suspended in a buffer solution in which the species to be inserted is dissolved. Bulk electroporation entails high voltages, however, and provides little control over the effectiveness of the process on individual cells due to the difficulty of achieving uniform exposure of all of the cells to the electric field. Overexposure can result in irreparable damage to the cells while underexposure will fail to produce pores in the cell membrane. The differences among cells in a single population are due in part to the cells themselves since the cells will vary in size and stage of growth, and some cells will be shielded from the electric field by other cells.

To address these problems, systems for single cell electroporation have been developed. A system for adherent cells, for example, using microelectrodes of carbon fiber that are placed 2-5 microns from the cells, has been reported by Lundqvist, J. A., et al., "Altering the biochemical state of individual cultured cells and organelles with ultramicroelectrodes," *Proc. Natl. Acad. Sci. U.S.A.*, 1998, 95, 10356-10360. A system for non-adherent cells using electrolyte-filled capillaries has been reported by Nolkrantz, K., et al., "Electroporation of Single Cells and Tissues with an Electrolyte-Filled Capillary," *Analytical Chemistry*, 2001, 73, 4469-4477. Systems using micropipettes have been reported by Haas, K., et al., "Single-cell electroporation in gene transfer in vivo," *Neuron*, 2001, 29, 583-591, and by Rae, J. L., et al., *Eur. J Physiol.*, 2002, 443, 664-670. A system using a specially designed microelectroporation chip is described by Huang, Y., et al., "Micro-Electroporation: Improving the Efficiency and Understanding of Electrical Permeabilization of Cells," *Biomed. Microdevices*, 1999, 2:2, 145-150. A system that draws a small section of the cell membrane into a channel and then applies an electric field between two electrodes, one inside and the other outside the channel, is reported by Ionescu-Zanetti, C., et al., United States Patent Application Publication No. US 2007/0243523 A1, "Methods and Apparatus for Manipulation of Particle Suspensions and Testing Thereof" (Oct. 18, 2007). Additional disclosures of single-cell electroporation of possible relevance to the present invention are those of Khine, M., et al, "Single Cell Electroporation Chip," Lab Chip, 2005, 5, 58-43; Khine, M., et al., "Single-cell electroporation arrays with real-time monitoring and feedback control," *Lab Chip,* 2007, 7, 457-462; and Nolkrantz, K. et al., "Functional Screening of Intracellular Proteins in Single Cells and in Patterned Cell Arrays Using Electroporation," *Analytical Chemistry,* 2002, 74, 4300-4305.

SUMMARY OF THE INVENTION

The present invention resides in a method and apparatus for performing electroporation on a multitude of cells by focusing an individual electric field on a portion of preselected size of the membrane of each cell, the size being the same for each cell regardless of any differences in the sizes of the cells themselves. To achieve these results, the electrodes are placed in micro-sized openings, referred to herein as "through-passages," in a vessel wall, and a suspension of the cells in a liquid solution of the exogenous species is placed in the vessel. When a pressure differential is imposed across the wall and through the openings, the cells are drawn against the wall to plug the openings, and portions of the cell membranes protrude into the openings to enter the region where the electrodes reside. Each opening contains two electrodes positioned on opposite sides of the opening, i.e., across the axis of the through-passage, and the electrodes are embedded in the walls of the opening at a location that is spaced apart from the mouth of the opening at the surface contacting the remainder of the cell. Each pair of electrodes thus defines a gap across the width of the opening, and the dimensions of the gap are the same in all openings.

In a preferred embodiment, the vessel wall is a laminated or otherwise layered structure whose layers include an insulator layer with an array of micro-sized openings, a substrate layer that contains electrically conductive traces and an array of micro-sized openings that are aligned with the openings in the insulator layer, and a vacuum source arranged to draw a vacuum through the substrate and the insulator layer. The electrical traces reside in the surface of the substrate where the substrate is laminated to the insulator layer, preferably at or near the interface between the substrate layer and the insulator layer. The openings in each layer are preferably arranged in rows, and the electrode traces are arranged in pairs with one member of each pair on each of opposing sides of each row of openings such that a single pair of traces serves as the two electrodes for all openings in the row. The openings in the substrate layer are preferably slightly smaller than those in the insulator layer. The decrease in size of the openings at the interface between the two layers serves as a shoulder or partial obstruction to cells that are drawn into the aligned openings when a pressure differential is imposed across the layers, the shoulder causing the cells to lodge at the interface. The diameters of the openings in the insulator layer are equal to or smaller than those of the typical cell, and thus a cell drawn into an opening will either substantially fill the opening without distortion or be compressed by the opening. In either case, the cell spans the width of the opening to contact all sides of the opening, while extending far enough into the opening to contact the electrodes. When an electric potential is applied between a pair of electric traces, only that portion of each cell membrane that is between the electric traces on either side of the opening is exposed to the electric field. Thus, by having openings of uniform size and length and by applying uniform pulses across all pairs of electric traces, together with a sufficient pressure differential to draw each cell into an opening and into contact with the traces, the apparatus exposes the same membrane area on each of a multitude of cells to the same electric field intensity, thereby achieving a uniformly porated area of uniform size on each cell of the cell population.

Further features, variations, implementations, and preferred embodiments of the invention are described below.

DETAILED DESCRIPTION OF THE INVENTION AND PREFERRED EMBODIMENTS

Figure 1:
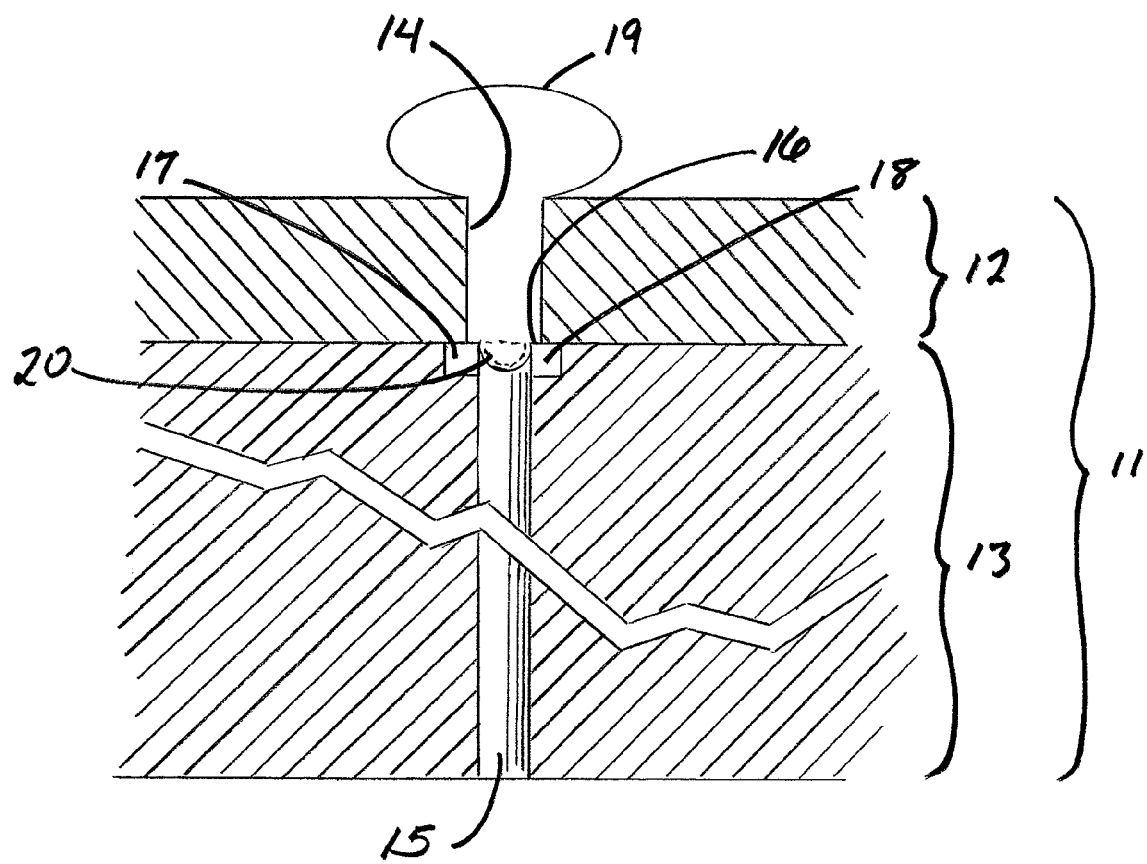
FIG. 1 is a cross section of the two layers of a layered structure in which a through-passage is formed in accordance with the present invention.

The present invention is useful in the electroporation and transfection of membrane-encased structures in general, examples of which are liposomes, vesicles, and all kinds of biological cells, of varying sizes. The term "cell" is used generically herein for convenience to denote any of these membrane-encased structures. The diameter of each through-passage, or at least of the mouth of the through-passage through which the cell enters the through-passage, will preferably be equal to or less than the diameter of a single cell being permeabilized. The portion of the through-passage in which the electrodes reside is preferably less than the cell diameter so that the normal geometry of the cell will be distorted and the cell will be laterally compressed once drawn inside the opening. The through-passages can thus be sized for particle types of cells, or for particular cell size ranges. For cells with a known diameter size range, the optimal opening at the entry to the through-passage, and through the insulator layer in embodiments that contain such a layer, will be approximately equal to or slightly less than the lower limit of the cell size range. Thus, for biological cells with diameters in the range of approximately 10-20 microns, through-passages with diameters in the range of about 5 microns to about 10 microns are preferred. For cells of 10-20 microns and for laminated structures that contain both an insulator layer at the entry side and a substrate layer, the optimal passage through the insulator layer will have a diameter of about 10 microns, while the diameter of the passage through the substrate layer will optimally be 1-5 microns less than that of the opening in the insulator layer. For example, an insulator layer with openings that are 10 microns in diameter can be laminated to a substrate with openings that are about 8 microns in diameter. The center-to-center distances between adjacent through-passages will preferably be great enough to avoid contact of cells protruding from adjacent openings. Thus, for cells of diameters within the range of 10-20 microns, the center-to-center distances between adjacent through-passages will preferably be at least about 30 microns, more preferably from about 30 microns to about 100 microns. The spacing will determine how many such openings can be included in a single device, and the number of openings will also be controlled by a variety of external factors, either those reflecting the geometry of the device itself or those related to other components of the instrumentation in which the device is incorporated. A regularly spaced array, such as a rectangular array or a staggered array, will provide a known number of openings and is readily formed.

In terms of the laminated-wall embodiment, the depth of each opening in the insulator layer, and hence the thickness of the insulator layer, can likewise be selected to accommodate particular cells or cell types. Cells that will undergo a relatively large degree of compression to enter the opening will function best with an insulator layer that is relatively thin, such as 10 microns or less, or 5 microns or less in some cases, whereas for cells that fit more readily inside the opening and can enter the opening more easily, a thicker insulator layer can be used and the apparatus as a whole may be simpler to fabricate as a result. A thicker insulator layer can also provide greater control over the electrical fields. Thus, for biological cells of 10-20 microns in diameter, the thickness of the insulator layer in one embodiment can be 25 microns. In most cases, however, a thickness range of from about 3 microns to about 300 microns, preferably from about 3 microns to about 100 microns, and most preferably from about 5 microns to about 50 microns, will be appropriate. The spacing among the openings in the substrate layer will be identical to that in the insulator layer. The two layers can be fused together during manufacture, or they can be separate pieces that are joined by the user prior to use. In the latter case, proper alignment of the openings can be achieved by fiducials, whose design and use will be readily apparent to those skilled in the art, particularly the art of microfluidics.

The electrical traces are arranged in the substrate layer such that a pair of traces is exposed to each opening in the substrate layer. Any cell protruding into or through the interface between the insulator and substrate layers will then be in physical contact with both traces, or if not in actual physical contact, then close enough that the resulting electric field exposure is the same as that which would occur if actual contact were made. When a voltage is then applied between the electrodes, the portion of the cell that is exposed to the resulting electric field is thus the portion intersecting with, or very near to, the interface, and poration occurs in this portion of the cell membrane only. When optimally positioned, therefore, the traces are at the interface, and specifically at the rim of each opening in the substrate layer at the surface directly opposite the insulator layer.

The thickness of the substrate layer is of less significance than the thickness of the insulator layer since the electroporation will occur only at the interfacial region between the layers. The substrate layer serves to transmit the vacuum and the resulting pressure differential, to draw the cells into the openings in the layers, and to release the vacuum once the voltage pulsing across the electrodes has terminated. The substrate layer can also serve to impart rigidity to the insulator layer. Accordingly, the substrate layer in preferred embodiments is thicker than the insulator layer, and thicknesses in these embodiments can range from 100 microns to 1,000 microns.

Conventional materials of construction used in microfluidics devices and in semiconductor or chip fabrication can be used for the two layers. The insulating layer can, for example, be of any electrically insulating polymer, and the selection may be governed by the desired thickness of the layer and the manner in which it is deposited on the substrate if it is indeed formed by deposition. Examples of materials for the insulating layer are polycarbonate, polysilicon, and polydimethylsiloxane (PDMS). The portions of the through-channels extending through the insulator layer can be formed by conventional techniques, such as for example mechanical punching, etching, laser punching, or photolithography. The substrate layer can be formed of the same polymers listed for the insulator layer above plus glass and silicon, and the portions of the through-channels extending through substrate can be formed by the same methods as those used in the insulator layer. The electrical traces can be formed by conventional manufacturing techniques used in the semiconductor industry, such as for example etching followed by plating. Alternatively, conductive glass or conductive films can be used. For substrate layers of silicon, the traces can also be formed by solid state methods known in the art.

The Figures accompanying this specification illustrate an example of an implementation of the concepts and principles of this invention.

FIG. 1 is a cross section of a portion of an electroporation apparatus 11 in accordance with the invention. The insulator layer 12 is shown as the upper layer in this view and the substrate layer 13 as the lower layer. The substrate layer 13 is shown in segmented form since its thickness is much greater than that of the insulator layer 12. The insulator layer 12 has an opening or through-passage 14 that is 10 microns in diameter, and the substrate layer 13 has an opening or through-passage 15 that is 8 microns in diameter and axially aligned with the opening in the insulator layer 12. The difference in diameters creates a shoulder 16 that encircles the through-passage 15. Also shown in the substrate layer 13 adjacent to the upper surface of the layer, and hence the interface between the two layers, are two electrical traces 17, 18, shown in cross section and positioned on opposite sides of the rim of the passage 15 through the substrate layer. A cell 19 on which electroporation is to be performed is shown, with a portion of the cell extending entirely through the opening 14 in the insulating layer and protruding a short distance into the opening 15 in the substrate layer, while the remainder of the cell remains above the insulator layer 12. The cell 19 is held in this location by a pressure differential across the two layers, formed by a partial vacuum imposed on the region underneath the substrate layer 13. The shape of the cell is distorted by the force of the pressure differential against the confining dimensions of the openings 14, 15. The portion of the cell that will be porated when a potential is imposed between the electrical traces 17, 18 and is shown in dashed lines 20. As noted above, this portion is the same size for each cell, regardless of the volume or shape of the remainder of the cell.

Figure 2:
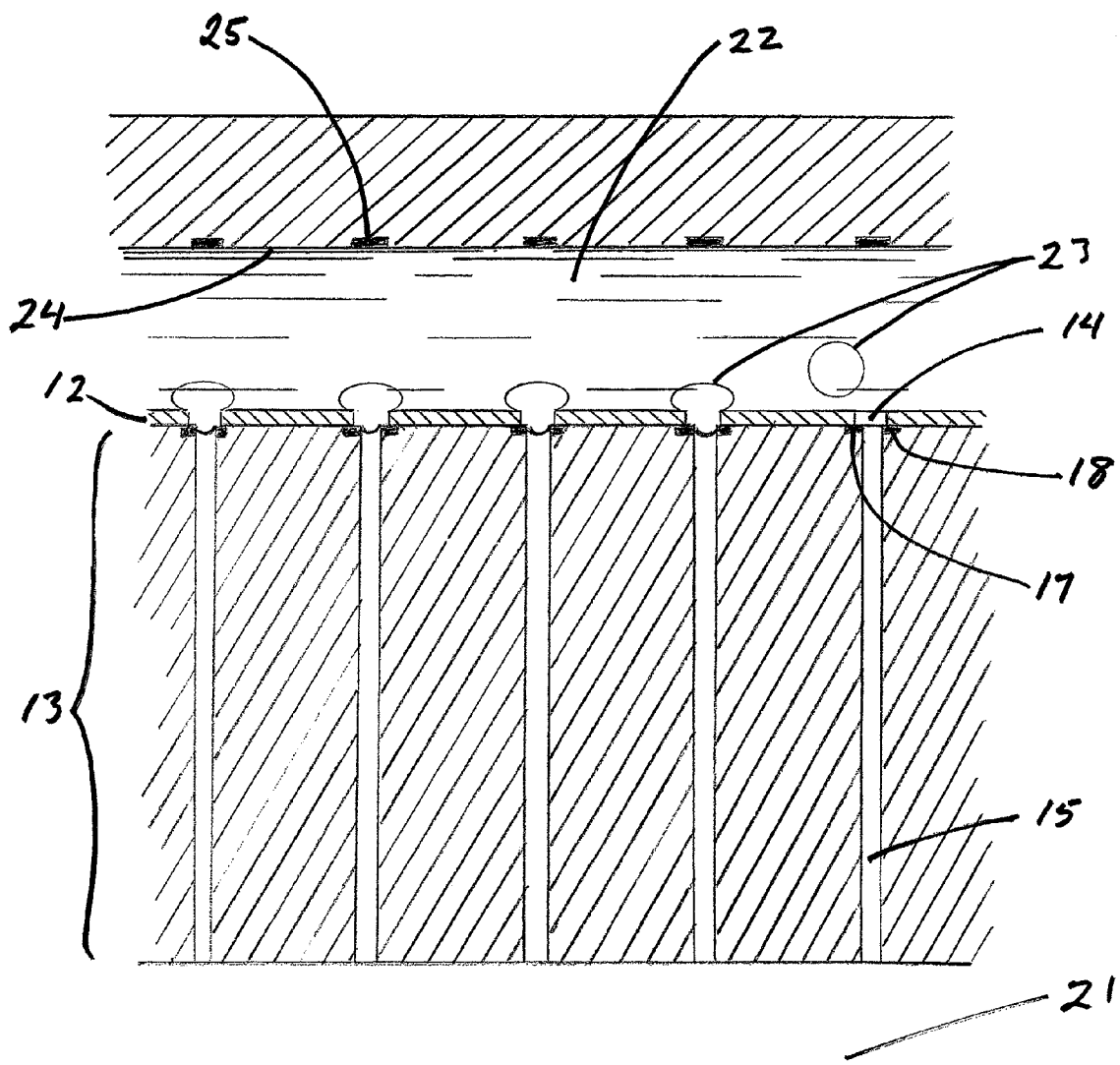
FIG. 2 is a cross section of an electroporation device incorporating the layered structure of FIG. 1.

FIG. 2 is a cross section of an electroporation apparatus incorporating the portion shown in FIG. 1. As in FIG. 1, the apparatus includes the insulator layer 12 and a substrate layer 13, and the openings 14, 15 through the two layers, respectively. The openings 14 in the insulator layer aligned with the slightly smaller openings 15 in the substrate layer to form through-passages extending through both layers with shoulders at the interfaces of the two layers and the electrical traces 17, 18 in the substrate layer at the interface. At the substrate layer side, the through-passages open into a chamber 21 on which a vacuum can be drawn, and at the insulator layer side the through-passages open into a channel or chamber 22 containing the cell suspension. The cells 23 are used as a suspension in an appropriate carrier liquid, in which is dissolved the molecular species that will penetrate the cell membrane during the procedure. The dilution of the cells in the suspension and the volume of the suspension are such that the number of cells in a single batch of the suspension is approximately equal to or less than the number of through-passages formed by the combined passages 14, 15 in the insulator and substrate layers 12, 13. Each cell in the batch will then be drawn into one of the through-passages. Embedded in the opposing wall 24 of the cell suspension chamber 22 are a separate series of electrical traces, whose function is described below.

Figure 3:
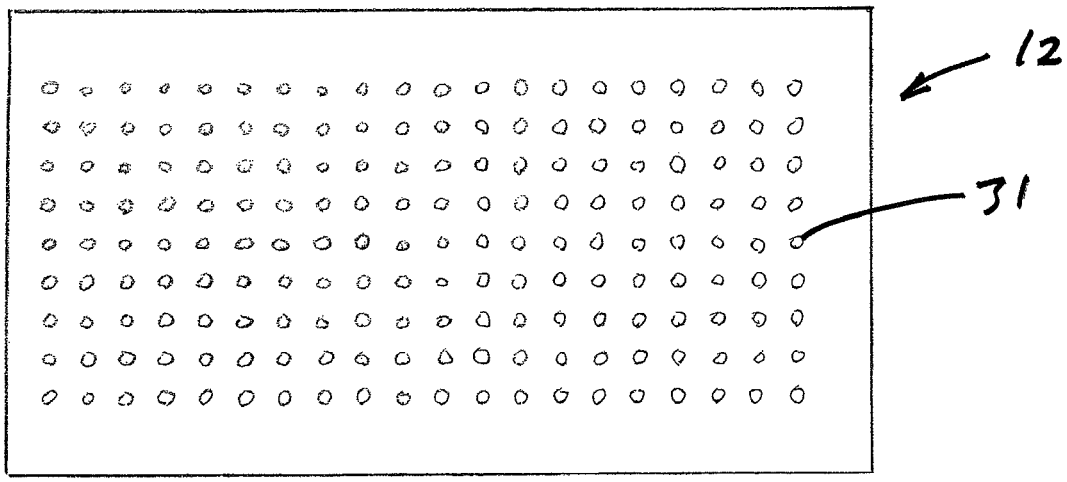
FIG. 3 is a top view of one of the two layers of the layered structure of FIGS. 1 and 2.

FIG. 3 is a top view of the insulator layer 12 of FIG. 2. The openings 31 to the passages through the layer form an array across the surface of the layer, and although a relatively small number of openings is present in the depicted layer for purposes of clarity, it is contemplated that with a center-to-center spacing of 50 microns between the openings, for example, a single rectangular device can contain approximately 106 openings in an area of 4 inches by 4 inches (10.2 cm×10.2 cm).

Figure 4:
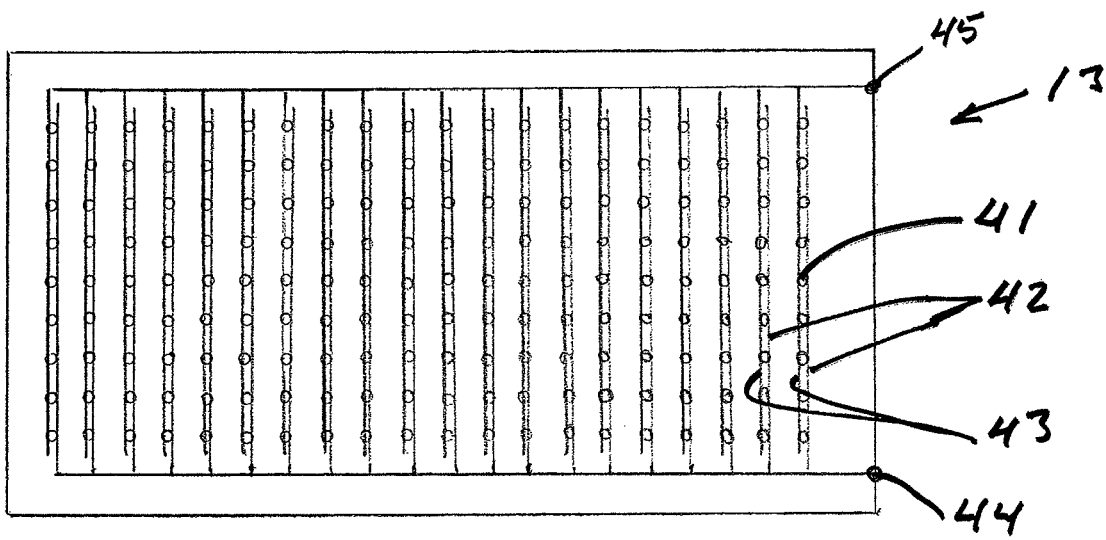
FIG. 4 is a top view of the other of the two layers of the layered structure of FIGS. 1 and 2.

FIG. 4 is a top view of the substrate layer 13 of FIG. 2. The openings 41 in the surface of the substrate layer are identical in number to those of the insulator layer and are arranged in an identically spaced array. The electrical traces are shown as two grids 42, 43, each grid consisting of parallel traces extending the length of one column of openings 41. The traces of one grid 42 contact one side of each opening 41 in each column and those of the other grid 43 contact the other side of the same openings. The first grid 42 is connected to a single electrical junction 44 and the second grid 43 is connected to a separate electrical junction 45. Voltage pulsing is applied across all openings by producing voltage pulses between the two junctions.

Returning to FIG. 2, a typical protocol will begin with the placement of the cell suspension in the chamber 22 adjacent to the insulator layer 12, while a vacuum is drawn on the chamber 21 adjacent to the substrate layer 13. The vacuum need only be strong enough to create a pressure differential across the combined layers to draw the cells 23 into the openings 14 in the insulator layer. In most cases, a pressure differential of from about 0.3 to about 5 pounds per square inch, or preferably from about 0.5 to about 3 pounds per square inch, will suffice. The degree of vacuum is preferably low enough that no significant amount of the cell suspending liquid (i.e., the buffer solution) will enter the vacuum chamber 21. The surface tension of the buffer solution and the small diameter and relatively long length of the openings 15 in the substrate layer further prevent the buffer solution from passing into the vacuum chamber.

The vacuum is maintained as voltage pulses are imposed across the paired traces. Pulses of magnitudes and durations that are commonly used in electroporation can be used. After the pulsing, the vacuum is released, allowing the cells 23 to drift back out of the openings 14 and into the bulk of the buffer solution in the chamber 22. Dissolved in the buffer solution will be the species that is to pass through the porated cell membrane and enter the cell. As known among those familiar with electroporation, proteins, peptides, drugs, and genetic material are examples of the types of species that can be introduced into cells in this manner. Once the porated cell is released from the insulator layer openings 14, the cell will typically remain porous long enough for the species to penetrate the cell membrane by diffusion. Penetration of the membrane can be accelerated or enhanced, however, by imparting an electric charge to the suspension chamber electrodes 25 of a polarity that will urge the species to migrate toward the electrodes 25 in an electrophoretic effect. Since the porated section of each cell will be on the side facing the insulator layer 12, i.e., the lower side in the view shown in the Figure, molecules of the species positioned between a cell and the insulator layer 12 will migrate into the cell under the electrophoretic effect. In the meantime, the cell, by its natural processes, will be repairing the membrane to close the pores, and the migration of the species through the pores, whether with or without assistance from the upper electrodes 25, will migrate through the pores before the pores are fully repaired.

An optional feature of the invention is the use of the grids 42, 43 (FIG. 4) to sense the presence of the cells at the openings and likewise to sense the number of openings that have been closed with cells lodged across or inside them. Sensing is readily achieved by measurements of electrical resistance between the pairs of traces, since a significant change in resistance at each pair will occur when the pair is spanned by a cell. The resistance measurements can be coordinated with the electroporation pulsing.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or otherwise known in the art and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. Apparatus for transfection of cells, said apparatus comprising:
    a vessel bordered by an internal vessel wall perforated with a plurality of through-passages, each through-passage having an axis transverse to said vessel wall, each through-passage further having internal walls in which are embedded a pair of electrodes on opposite sides of said axis, each pair of electrodes defining a gap of dimensions that are uniform among all of said through-passages, and each through-passage having an internal shoulder with said electrodes positioned adjacent to said shoulder;
    means for imposing a pressure differential through said through-passages sufficient to draw biological cells from a biological cell suspension retained in said vessel against said through-passages and to cause said biological cells to protrude into said through-passages and into said gaps; and
    means for imposing an electric potential between each pair of electrodes.

2. The apparatus of claim 1 wherein said internal vessel wall has an internal surface and said electrodes are electrically insulated from said internal surface.

3. The apparatus of claim 1 wherein said internal vessel wall is a laminated structure comprising first and second laminae, said first lamina being electrically insulating and said second lamina having said electrodes embedded therein.

4. The apparatus of claim 1 wherein said through-passages are arranged in rows and the electrodes in the internal walls of the through-passages in each single row are conductive traces extending the length of said row, said row thereby having two said traces, one on each of opposing sides of said row.

5. The apparatus of claim 1 wherein said through-passages each have a diameter of a maximum of about 10 microns.

6. The apparatus of claim 1 wherein said through-passages each have a diameter of from about 5 microns to about 10 microns, and said through-passages are spaced to have center-to-center distances of from about 30 microns to about 100 microns.

7. The apparatus of claim 1 further comprising means for drawing said cells away from said internal vessel wall.

8. The apparatus of claim 7 wherein said internal vessel wall is defined as a first vessel wall, and said means for drawing said cells away from said internal vessel wall is an electrode embedded in a second vessel wall opposite said first vessel wall.

* * * * *